| United States Patent [19] | [11] Patent Number: 4,833,274 |
|---|---|
| Caporiccio et al. | [45] Date of Patent: May 23, 1989 |

[54] PERFLUOROALKANES AND HALOPERFLUOROALKANES, THEIR PERCURSORS AND PROCESS FOR THEIR SYNTHESIS

[75] Inventors: Gerardo Caporiccio; Gianangelo Bargigia, both of Milan; Claudio Tonelli, Concorezzo/Milan; Vito Tortelli, Milan, all of Italy

[73] Assignee: Ausimont S.p.A., Milan, Italy

[21] Appl. No.: 149,902

[22] Filed: Jan. 28, 1988

Related U.S. Application Data

[63] Continuation of Ser. No. 847,743, Apr. 3, 1986, abandoned.

[30] Foreign Application Priority Data

Apr. 4, 1985 [IT] Italy .............................. 20235 A/85

[51] Int. Cl.$^4$ ...................... C07C 17/28; C07C 19/07; C07C 19/08
[52] U.S. Cl. .................... 570/137; 570/125; 570/139; 514/832; 252/570; 228/40
[58] Field of Search ................ 570/137, 125

[56] References Cited

U.S. PATENT DOCUMENTS

| 2,490,764 | 12/1949 | Benning et al. | 570/134 |
|---|---|---|---|
| 3,083,238 | 3/1963 | Hauptschein et al. | 570/139 |
| 3,377,390 | 4/1968 | Rondestvedt | 570/139 |
| 3,883,604 | 5/1975 | Rudolp et al. | 570/139 |
| 3,956,412 | 5/1976 | Knell | 570/172 |
| 4,067,916 | 1/1978 | Jaeger | 570/139 |

FOREIGN PATENT DOCUMENTS

| 20282 | 8/1968 | Japan | 570/137 |

*Primary Examiner*—J. E. Evans
*Attorney, Agent, or Firm*—Stevens, Davis, Miller & Mosher

[57] ABSTRACT

New perfluoroalkanes and haloperfluoroalkanes, having low melting point and high thermal and chemical stability, constituted by preferably branched perfluorinated and haloperfluorinated chains, obtained by starting from precursors containing two halogen atoms equal to or different from each other, one of them necessarily being an iodine atom, which are reacted with $C_3F_6$ and possibly subsequently halogenated with either fluorine or chlorine or bromine.

1 Claim, No Drawings

PERFLUOROALKANES AND HALOPERFLUOROALKANES, THEIR PERCURSORS AND PROCESS FOR THEIR SYNTHESIS

This application is a continuation of application Ser. No. 847,743, filed Apr. 3, 1986, now abandoned.

BACKGROUND OF THE INVENTION

1. Field of the Invention

The present invention relates to new perfluoroalkanes and haloperfluoroalkanes, characterized by having a low melting point and high thermal and chemical stability, constituted by preferably branched perfluorinated or haloperfluorinated chains.

More particularly, the invention relates to new preferably branched perfluoroalkanes and haloperfluoroalkanes, obtained from precursors characterized by containing in their chain two halogen atoms equal to or different from each other, one of which necessarily being a iodine atom.

A further purpose of the present invention is to provide a process for the synthesis of said preferably branched perfluoroalkanes or haloperfluoroalkanes, by a method which can be easily implemented on an industrial scale.

2. Description of the Prior Art

Perfluoroalkanes are known which are obtained by means of the Phillips electrochemical fluorination process (U.S. Pats. Nos. 3,511,760 and 3,511,761), which can be suitably used for the synthesis of several compounds, among which perfluoroalkanes too. The limitation of this process derives both from the fact that it results expensive as regards the equipment installation and, above all, the energetic viewpoint, and from the fact that it allows conveniently fluorinating only compounds having a low molecular weight. pounds (products of up to six carbon atoms).

Also perfluoroalkanes obtained by anionic aligomerization of perfluoroolefins (U.S. Pat. Nos. 3,917,724 and 3,962,358) and subsequent fluorination of the double bonds are known, but the useful products which can be obtained are perfluoroalkanes of either 6 or 9 carbon atoms, whilst the other oligomers obtainable in practice show a high branching degree, which reduces the stability of such products (see J. Fluor. Chem. (1981) 18 417).

Perfluoroalkanes are furthermore known, which are obtained by starting from aromatic hydrocarbons, such as, e.g., toluene, by fluorination with $CoF_3$, but this synthesis requires the use of particularly sophisticated equipment, withstanding both the fluorine used to regenerate the $CoF_3$ which is reduced during the synthesis, and the high temperatures normally required for their synthesis. Moreover, as the reaction proceeds, the replacement of the hydrogen atoms of the hydrocarbon used as the precursor of the perfluorinated compounds to be prepared, becomes more and more difficult, so that a not completely fluorinated fluid is obtained, containing byproducts still having hydrogen atoms.

The presence of these byproducts decreases, among others, the thermal stability, the thermal and chemical inertia of the product, thus limiting the application field of these fluorinated fluids.

Moreover, the methods for the separation of said not completely fluorinated byproducts are very expensive and difficult to be carried out.

Iodoperfluoroalkanes can be obtained by telomerizing tetrafluoroethylene with such telogens as $CF_3I$, $C_2F_5I$, $C_3F_7I$.

In this case, their preparation results anyway difficult, as $CF_3I$ can be obtained ony by the decomposition of $CF_3COOAg$ in the presence of iodine (Hunsdiecker reaction), and for the other two products the use of IF is required, which is notoriously difficult to be synthetized and handled.

THE PRESENT INVENTION

By the present invention, the following purposes are essentially achieved:

(1) providing versatile reactant products having the structure of preferably branched diiodoperfluoroalkanes, easily convertible into the corresponding chloro- or bromo-or fluoro-derivatives, by partial or total substitution of the two iodine atoms;

(2) allowing the preparation of moderately branched perfluoroalkanes by means of a very simple method, avoiding both the process of electrochemical fluorination and a complete fluorination of the starting product by using elemental fluorine only;

(3) producing preferably branched dichloro- or dibromoperfluoroalkanes, having the chlorine or bromine atoms bonded to not adjacent carbon atoms;

(4) producing perfluoroalkanes substituted on two notadjacent carbon atoms with two halogen atoms different from each other, and selected among I, Br, Cl, F; in case that one of the two halogens is fluorine, the chain must be branched.

The presence of a moderate branching in the molecular structures of the products of the invention is recommendable because, as it has been noticed, the products remain liquid within wider temperature ranges, although their boiling temperature does not excessively vary, and without their stability be decreased, as it occurs with the highly branched products. For example, as it is described in "Chemistry of Organic Fluorine Compounds", M. Hudlicky, (1976), page 532, the linear perfluoroparaffin with 9 carbon atoms has melting point and boiling point of respectively −20° C. and +125° C., whilst perfluoro-2,4-dimethyl-heptane has respectively −77° C. and +124° C. (these latter data result from our measurements).

The products according to the invention have the general formula:

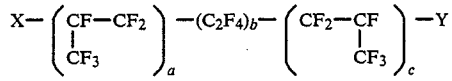

wherein:
a and c, equal to or different from each other, are integers ranging from 0 to 4 and preferably from 0 to 2, their sum being not lower than 1 and not greater than 6, preferably not greater than 3;
b is an integer ranging from 1 to 5, preferably from 1 to 3;
the sum a+b+c is not greater than 8, preferably not greater than 5;
X and Y, equal to or different from each other, can be iodine, bromine, chlorine or fluorine; with the limitations:
that X and Y can be contemporaneously fluorine only in case in which at least one of the two indexes a and c is equal to or greater than 2;

that X is not fluorine when a=1 and c=0; that Y is not fluorine when c=1 and a=0;

that Y cannot be I when X=F and c=0;

that X cannot be I when Y=F and a=0.

The —$C_2F_4$— units can be present in the molecular structure also alternated to the —$CF_2$—$CF(CF_3)$— units.

The diiodides according to the present invention are obtained according to the reaction scheme:

$$I(C_2F_4)I + (b - 1) C_2F_4 \longrightarrow I(C_2F_4)_b I$$

$$I(C_2F_4)_b I + (a + c) C_3F_6 \longrightarrow$$

$$I-\left[\begin{array}{c}CF-CF_2\\|\\CF_3\end{array}\right]_a-(C_2F_4)_b-\left[\begin{array}{c}CF_2-CF\\|\\CF_3\end{array}\right]_c-I$$

The corresponding difluorides are obtained by fluorination with, e.g., elemental fluorine, according to the following reaction:

$$I-\left[\begin{array}{c}CF-CF_2\\|\\CF_3\end{array}\right]_a-(C_2F_4)_b-\left[\begin{array}{c}CF_2-CF\\|\\CF_3\end{array}\right]_c-I + F_2 \longrightarrow$$

$$F-\left[\begin{array}{c}CF-CF_2\\|\\CF_3\end{array}\right]_a-(C_2F_4)_b-\left[\begin{array}{c}CF_2-CF\\|\\CF_3\end{array}\right]_c-F$$

The dichlorides and the dibromides are obtained in a similar way, by treating the above indicated diiodides with respectively elemental chlorine or bromine.

The products according to the present invention, wherein either X or Y is iodine, and the other is fluorine, chlorine or bromine, are obtained by partial halogenation of the above mentioned diodides, and fractionating by distillation the reaction mixture obtained. An alternative method consists in using as the starting telogen $ClC_2F_4I$ or $BrC_2F_4I$, the preparation of which is disclosed in the Italian Patent Application No. 19652 A/85, in this case however the insertion of the branched groups $$-CF_2-CF-\\|\\CF_3$$

only takes place on the iodine containing chain side.

The products according to the invention, wherein one of the two halogen atoms X or Y is fluorine, and the other one is either chlorine or bromine, can be obtained by chlorinating or brominating products in which one of the two halogens X or Y is fluorine, and the other one is iodine.

The products wherein one of the two halogens X or Y is chlorine and the other one is bromine are obtained by brominating products in which X or Y is chlorine, and the other is iodine.

Examples of products according to the present invention are:

$$I-(C_2F_4)_2-CF_2-CF-I\\|\\CF_3$$

-continued $$I-CF-CF_2-(C_2F_4)_2-CF_2-CF-I\\|\quad\quad\quad\quad\quad\quad\quad\quad\quad\quad|\\CF_3\quad\quad\quad\quad\quad\quad\quad\quad\quad\quad CF_3$$

$$I-CF-CF_2(C_2F_4)_2-\left[CF_2-CF\atop|\atop CF_3\right]_2-I\\|\\CF_3$$

$$Cl-CF-CF_2-(C_2F_4)_2-CF_2-CF-Cl\\|\quad\quad\quad\quad\quad\quad\quad\quad\quad\quad|\\CF_3\quad\quad\quad\quad\quad\quad\quad\quad\quad\quad CF_3$$

$$I-(C_2F_4)_2-\left[CF_2-CF\atop|\atop CF_3\right]_2-I$$

$$I-CF-CF_2-(C_2F_4)_3-\left[CF_2-CF\atop|\atop CF_3\right]_2-I\\|\\CF_3$$

$$I-(C_2F_4)_2-\left[CF_2-CF\atop|\atop CF_3\right]_3-I$$

$$I-(C_2F_4)_2-\left[CF_2-CF\atop|\atop CF_3\right]_4-I$$

$$I-(C_2F_4)_2-CF_2-CF-Br\\|\\CF_3$$

$$Cl-(C_2F_4)_2-CF_2-CF-Br\\|\\CF_3$$

$$Cl-CF-CF_2(C_2F_4)_2-\left[CF_2-CF\atop|\atop CF_3\right]_2-F\\|\\CF_3$$

$$F-CF-CF_2-C_2F_4-\left[CF_2-CF\atop|\atop CF_3\right]_2-F\\|\\CF_3$$

$$I-C_2F_4-CF_2-CF-C_2F_4-I\\|\\CF_3$$

$$Br-(CF_2CF_2)_2-CF_2-CF-Br\\|\\CF_3$$

According to the present invention, 1.2-diiodotetrafluoroethane $IC_2F_4I$ is telomerized first with $C_2F_4$ and then with $C_3F_6$ or with $C_3F_6$ alone, at a temperature comprised within the range of from 150° C. to 250° C., or at 45° C.–150° C. in the presence of peroxides, or also catalyzing by the metal ion/amine system, such as $Cu^+$/ethanol amine.

Also a mixture of $C_3F_6$ with $C_2F_4$ can be used, in this case —$C_2F_4$— units alternating in the chain with $$-CF_2-CF-\\|\\CF_3$$

units being obtained.

The fluorinations can be carried out with elemental fluorine in the presence or in the absence of inert solvents, with or without U.V. radiations, or with fluorides of metals having their maximum oxidation number, however operating under conditions considerably milder than those of the processes known in the art.

The chlorination and the bromination can be carried out with elemental chlorine or respectively bromine, in autoclave, within the temperature range of from 100° C. to 250° C., or by bubbling the gaseous halogen into the iodides used as the starting materials, maintained at 100° C.–200° C., or also in the presence of U.V. radiations between 0° C. and +50° C.

The products according to the present invention are suitable to be used for a very large number of applications. So, e.g., the completely fluorinated compounds (X and Y=F) are inert fluids, to be used as dielectric fluids, and as fluids for electronics testing, e.g., in the Thermal Shock Test, the Burn in Test, the Gross Leak test, and for the "Vapour Phase Soldering", and finally as oxygen carriers biocompatible with blood.

The dichlorides, having the two chlorine atoms relatively far from each other, and the monochlorides (X=Cl, Y=F or vice-versa) are stable, and can be used for some of the applications of the perfluorinated compounds (X and Y=F), when the use conditions are not too severe, as well as coolants for electronic circuits.

The dibromides and monobromides (with X=Br and Y=F, or vice-versa) can be used in the medical field as radiations shields, or as flame-proofing compounds; moreover, because of the high density due to the presence of bromine, they can be used as fluids for the filling of submarine cables, or as fluids for gyroscopes.

The diiodides, as seen, constitute the starting materials for the production of the hereinabove mentioned halogenated compounds.

The following Examples are supplied to the purpose of illustrating the present invention, and they are not to be intended as limitative of the application possibilities thereof.

EXAMPLE 1

Into a 250-ml Inconel autoclave 53 g (=0.12 mol) of $I(C_2F_4)_2I$ obtained, according to known techniques, by telomerization of $C_2F_4$ with $IC_2F_4I$, and then 80 g (=0.53 mol) of $C_3F_6$ are charged.

The mixture is heated at 200° C. for 16 hours, under stirring. The pressure increases up to 50 abs.atm, and then progressively decreases, during the proceeding of the reaction, down to 40 abs.atm. After cooling, the excess of $C_3F_6$ is discharged, and 63 g are recovered of crude product, which is washed with a diluted solution of sodium thiosulphate.

The organic layer is fractionated by rectification under 1 torr, with adiabatic column, and with reflux ratio 4:1. As lower boiling products, 26.5 g of product corresponding to the unreacted $I(C_2F_4)_2I$, and moreover two fractions, A and B, with boiling point of 42° C. and 72° C. respectively, in the amount of 28.5 and 7 g are collected. In the boiler 1 g remains of residual product.

On the basis of the analytical data resulting from gas-chromatographic analysis (G.C.) and from $^{19}F$-N.M.R. ($CFCl_3$, ppm), the A and B fractions result thus constituted:

(A) One product, corresponding to the formula:

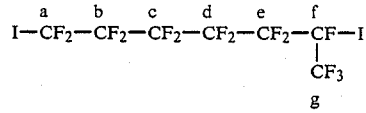

a=59 ppm
b=112 ppm
c+d=119–120 ppm
e=107 ppm
f=144 ppm
g=74 ppm (B) product which, on the basis of the gas-chromatographic analysis, shows two partially overlapping peaks in 1:1 ratio, with a retention time longer than the A one. On the basis of the 19F-N.M.R. analysis, the constituents of B result to be the following:

B.1 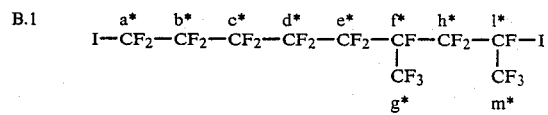

| | | |
|---|---|---|
| a* | = | 59 ppm |
| b* | = | 112 ppm |
| c* + d* + e* + h* | = | 110–120 ppm |
| f* | = | 177–184 (broad) ppm |
| g* | = | 70 ppm |
| l* | = | 144 ppm |
| m* | = | 73 ppm |

B.2 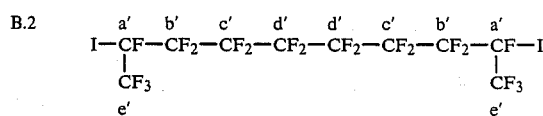

| | | |
|---|---|---|
| a' | = | 144 ppm |
| b' | = | 107 ppm |
| c' + d' | = | 119 and 120 ppm |
| e' | = | 74 ppm |

EXAMPLE 2

With the same equipment and modalities as of Example 1, 36 g (=0.079 mol) of $I-(C_2F_4)_2-I$ and 90 g (=0.6 mol) of $C_3F_6$ are charged. The reaction mixture is progressively heated up to 220° C., a pressure of 70 abs.atm being reached, and the reaction is carried out until the pressure decreases to 50 abs.atm; the temperature is then adjusted at 240° C. for 5 hours. The reaction mixture is then cooled, the gases are vented off and the product (55 g) is recovered and washed with an aqueous solution of sodium thiosulphate.

The fractionating is then carried out in a Spaltrohr-Fischer equipment, and the following fractions are obtained:

| Fraction 1 | 9.0 g | b.p. | 42° C.–43° C. under | 1 torr |
|---|---|---|---|---|
| Fraction 2 | 18 g | b.p. | 72° C. under | 1 torr |
| Fraction 3 | 14 g | b.p. | 99° C. under | 0.8 torr |
| Residue | 13.5 g. | | | |

On the basis of $^{19}F$-N.M.R. data, the fraction 1 corresponds to the product A of Example 1, the fraction 2 is constituted by the two B.1 and B.2 isomers of Example 1, in the weight ratio B.1/B.2=⅓. The fraction 3 is constituted by:

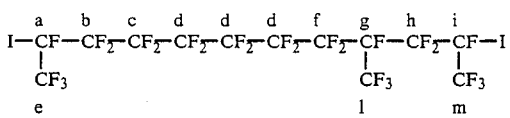

The chemical shifts a, b, c, d, and e correspond respectively to a', b', c', d', e' of compound B.2, and the chemical shifts f, g, h, i, l, m correspond respectively to e*, f*, h*, l*, g*, m*, of compound B.1.

The residue in the boiler, identified by gas-chromatography and $-^{19}$F-N.M.R. is constituted by 60% of the compound containing 4 —$CF_2CF(CF_3)$— units (two isomers), and by 40% of practically pure compound containing 5 —$CF_2CF(CF_3)$— units.

EXAMPLE 3

With the modalities as disclosed in Example 1, and with the same equipment, 73.5 g (0.16 mol) of I—$(C_2F_4)_2$—I and 130 g (0.87 mol) of $C_3F_6$ are reacted for 16 hours at 220° C.

The reaction product is recovered as described in Example 1, it being obtained in the amount of 115 g.

It results to be constituted by the following fractions, obtained by means of fractional distillation:

| | |
|---|---|
| Fraction 1: | 7.8% of unreacted I—$(C_2F_4)_2$—I |
| Fraction 2: | 28.8% of I—$(C_2F_4)_2(C_3F_6)$—I, identical to product A of Example 1. |
| Fraction 3: | 36.8% of I—$(C_3F_6)(C_2F_4)_2(C_3F_6)$—I I—$(C_2F_4)_2(C_3F_6)_2$—I, in the weight ratio 2.5/1, they correspond to products B.2 and B.1 of Example 1. |
| Fraction 4 | 18.6% of I—$(C_3F_6)(C_2F_4)_2(C_3F_6)_2$—I (identical to fraction 3 of Ex. 2) |
| | 1.9% of I—$(C_2F_4)_2(C_3F_6)_3$—I. |

The fraction 4 has been identified by N.M.R.-analysis. The chemical shifts are equal, apart from the integration, to the corresponding chemical shifts of the other peroducts already described in the foregoing Examples. The residue in the boiler, corresponding to 6.1%, is identified as an isomer mixture of molecular formula I—$(C_2F_4)_2(C_3F_6)_4$—I.

EXAMPLE 4

Into a 250-ml Inconel autoclave, 21 g (=0.028 mol)

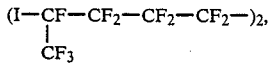

obtained as described in Example 1 are charged, together with 20 g of $Cl_2$ (=0.28 mol).

After 12 hours at 140° C., by operating as hereinabove described, 16 g of an organic phase is separated.

On G.C., a main product is identified, constituting 98% of the whole product, the residual 2% being unreacted starting material.

The product is purified as disclosed in Examples 1, by 19F-N.M.R. analysis the product is identified to be:

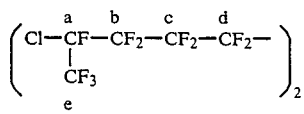

The chemical shifts are:
a=138 ppm
b=115 ppm
c+d=119–120 ppm.
e=78 ppm.

EXAMPLE 5

Into a tubular reactor of 5 cm of diameter, provided with a porous membrane on the bottom, with traps and condensers and suitable measurement and control systems, 150 ml are introduced of trichlorotrifluoroethane solvent, together with 22 g of the iodides obtained according to Example 2, and enriched by distillation, so that such products consist by more of 90% of the compound corresponding to fraction 3.

After spurging with $N_2$ and isotherming at 0° C., through the porous membrane a 2:1 by volume mixture of $N_2/F_2$ is flown at a flow rate of 3 l/h.

An initial colouring of the mixture, due to iodine, and an immediate decolouring due to the formation of iodine fluorides can be observed. At the same time, it can be observed also that, due to the exothermic character of the reaction, the temperature inside the reactor increases up to 17° C. When then the temperature decreases again, pure fluorine is flown for a further hour.

The product is neutralized with a 10% NaOH solution, and rectified. 14.1 g of perfluorinated product are isolated.

On the basis of G.C. and 19F-N.M.R. data, the iodides used as the starting material, which have been completely fluorinated, result absent.

The main product, with b.p. 194° C. results to be:

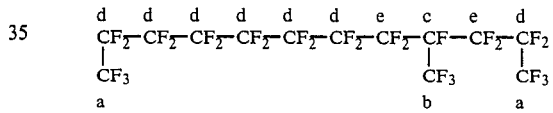

a=81 ppm
b=71 ppm
c=184 ppm
d=118–125 ppm
e=110 ppm

EXAMPLE 6

Into a 50-ml autoclave of AISI steel, 15 g (0.025 mol) of compound A of Example 1 and 20 g (0.125 mol) of $Br_2$ are introduced. The mixture is heated at 150° C. for 9 hours.

After cooling, the crude product (11.8 g) is recovered and washed, first with a 10% KOH solution, and then with 5% sodium thiosulphate solution. The product is rectified (b.p. 156° C.).

On gas-chromatographic analysis, one peak only is observed which, on the basis of N.M.R. analysis (chemical shifts and integration) results to be:

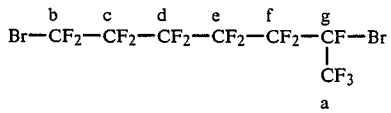

a=76 ppm
b=64 ppm
c=117 ppm
d+e=119–121 ppm
f=113 ppm

EXAMPLE 7

Into a 50-ml autoclave of AISI steel, 24 g (0.04 mol) of compound A of Example 1 and 12.8 g (0.08 mol) of Br$_2$ are introduced. The mixture is heated at 150° C. for 3 hours.

After cooling, the crude product is recovered and washed, first with a 10% KOH solution, and then with a sodium thiosulphate solution.

On gas-chromatographic analysis, two peaks in the ratio 3:1 are evidenced, none of which corresponds to the diiodide used as the starting material, and of which the one with shorter retention time is identical to that of Example 6, and namely:

$$Br-CF_2-CF_2-CF_2-CF_2-CF_2-\underset{\underset{CF_3}{|}}{CF}-Br$$

The product corresponding to the second peak is isolated by rectifying the reaction crude, and corresponds to:

$$I-CF_2-CF_2-CF_2-CF_2-CF_2-\underset{\underset{CF_3}{|}}{CF}-Br,$$

as, under N.M.R., it results that the chemical shifts and the integration are those foreseen on the basis of the corresponding A products of Example 1, and to those of the dibromide of Example 6.

We claim:

1. A haloperfluoroalkane of the formula:

$$X-\left(\underset{\underset{CF_3}{|}}{CF}-CF_2\right)_a-(C_2F_4)_b-\left(CF_2-\underset{\underset{CF_3}{|}}{CF}\right)_c-X$$

wherein:
  a and c, equal to or different from each other, are integers from 1 to 2 and their sum is not greater than 3;
  b is an integer from 2 to 3, the sum a+b+c being not greater than 4; and
  X is selected from the class consisting of iodine and bromine.

* * * * *